United States Patent [19]
Doat

[11] Patent Number: 5,817,330
[45] Date of Patent: Oct. 6, 1998

[54] LIQUID PARAFFIN OIL AND LACTULOSE-BASED HYPOCALORIC LAXATIVE JELLY AND METHOD FOR ITS PREPARATION

[76] Inventor: Bernard Doat, Résidence La Pléiade, 67 bd Jacques Millot, Angers, France, 49000

[21] Appl. No.: 727,623

[22] PCT Filed: Feb. 24, 1995

[86] PCT No.: PCT/FR95/00219

§ 371 Date: Feb. 4, 1997

§ 102(e) Date: Feb. 4, 1997

[87] PCT Pub. No.: WO95/22976

PCT Pub. Date: Aug. 31, 1995

[30] Foreign Application Priority Data

Feb. 25, 1994 [FR] France ..................... 94 02132

[51] Int. Cl.$^6$ ..................... A61K 9/00
[52] U.S. Cl. ............. 424/440; 424/441; 424/400; 424/451; 424/456; 426/271
[58] Field of Search ............. 424/400, 451, 424/456, 489, 440; 426/271

[56] References Cited

U.S. PATENT DOCUMENTS

| 5,604,207 | 2/1997 | DeFrees | ..................... 514/25 |
| 5,624,906 | 4/1997 | Vermeer | ..................... 514/23 |

FOREIGN PATENT DOCUMENTS

| 0 216 557 | 4/1987 | European Pat. Off. . |
| 0 478 837 | 4/1992 | European Pat. Off. . |
| 0 486 353 | 5/1992 | European Pat. Off. . |
| 2 618 351 | 1/1989 | France . |

OTHER PUBLICATIONS

Database WPI Week 9330, Derwent Publications Ltd., London, GB—Japanese Abstract JP,A,05 163 151, (Teikoku Seiyaku KK) 26 Jun. 1993.
"Traitement de la constipation" (Chaussade S., Guerre J.—Encyl. Med. Chir. Paris, Frace, Estomac–Intestin, 9071 A$^{10}$, Jun. 1985, 6pp.).
"Management of constipation" (Taylor R.—Br. Med. J., 1990, 300, 1063–64).
Vidal dictionary 1993.
"Transparent Emulsions of Some Essential Oils" (Whitmore W.F., R.E. Linehan—Ind. and Eng. Chemistry, 21, pp. 878–880, 1929.
"Gelatin", European Pharmacopeia, 2nd ed. 330, 1986.

*Primary Examiner*—Thurman K. Page
*Assistant Examiner*—D. Faulkner
*Attorney, Agent, or Firm*—Jean B. Barish

[57] ABSTRACT

Paraffin oil and lactulose-based jellied clear laxative emulsion containing from 75 to 85 parts by weight of liquid paraffin oil and from 25 to 15 parts by weight of an edulcorated lactulose aqueous solution. The invention also concerns a method for the preparation of said emulsion.

9 Claims, No Drawings

LIQUID PARAFFIN OIL AND LACTULOSE-BASED HYPOCALORIC LAXATIVE JELLY AND METHOD FOR ITS PREPARATION

This application is a continuation of PCT/FR95/00219 published Feb. 25, 1995.

SCOPE OF THE INVENTION

The object of the present invention is a new emulsified composition based on liquid paraffin oil and lactulose, produced in the form of a smooth, non-sticky jelly and intended for oral administration for the treatment of constipation in humans.

TECHNOLOGICAL BACKGROUND OF THE INVENTION

Constipation is a common pathological phenomenon which affects a considerable number of individuals with no real distinction as to sex or age. Recent publications indicate that this phenomenon chronically affects at least 10% of the French and British populations (Chaussade, S. and Guerre, J., Traitement de la constipation [Treatment of constipation], Encycl. Méd. Chir., Paris, France, Estomac-Intestin, 9071 A[10], 6-1985, 6 pp.; Taylor, R., Br. Med. J., 1990, 300, 1063–64), and that his percentage is even higher in the United States, Japan, and the northern European countries. It is also known that almost 50% of persons afflicted medicate themselves with laxatives, some of which are considered potentially dangerous.

Aside from the simplest cases, in which a dietary correction, in particular by administration of natural or dietetic fiber, is sufficient to correct the situation, it is frequently necessary to apply treatment by laxative means, one of the oldest and least harmful of which consists of ingestion of a mineral oil, more particularly liquid paraffin oil.

It is acknowledged that his oil, which is not absorbed, acts by way of its lubricating and emollient properties, thus promoting the evacuation of feces. This activity has been and still is widely utilized, since the French dictionary of pharmaceutical preparations (Dictionnaire Vidal, 1993, Editions du Vidal) lists a dozen preparations containing paraffin oils of various viscosities, alone or in association with other compounds, and offered in liquid or jellied form or as solid powders.

The liquid products are in fact most often pure or flavored paraffin oil. These are the least complex. However, aside from the practical difficulties in handling them, administering them to bedridden persons or to young children is tricky, since if difficulties in swallowing exist, involuntary inhalation of them can cause bronchial and/or pulmonary disorders. It is also known that in large doses, these liquid products entail undesirable risks of anal leakage and perianal irritation.

Jellied products are easier to handle. They are generally produced either by mixing liquid paraffin with semi-solid to solid paraffins, or by emulsifying liquid paraffin with an aqueous phase containing suitable excipients. Regarding emulsions of this kind, in 1921 Rector, in U.S. Pat. No. 1,389,161, described the means for producing transparent emulsions by adjusting the refractive index of the aqueous phase to that of the oil phase. W. FF. Whitmore and R. E. Linehan (Ind. and Eng. Chemistry, 21, pp. 878–880, 1929) generalize this teaching by describing modification of the refractive index of one or the other phase to obtain this transparent state. This principle has generated formulas for a variety of applications, including recently:

European patent application filed on Sep. 9, 1986 and published under no. 216 557 concerns translucent oil-in-water emulsions of semi-solid paraffin, similar in appearance to jelly and intended for application to the skin. Their aqueous phase contains a humectant agent, and the oil phase an agent suitable for the preparation of water-in-oil emulsions and semi-solid paraffin (m.p. >38° C.), to which a mineral oil is optionally added. In the Examples illustrating the invention, the oil phase does not exceed 70%, and the emulsifying agent specific to the water-in-oil emulsions is dissolved in the oil phase during preparation.

object of the French patent application filed on Jul. 20, 1987 and published under no. 2 618 351 is a jellied, transparent oil-in-water emulsion consisting of 50 to 80% by weight of a hydrophobic oily liquid, 0.5 to 5% of a water-soluble surfactant agent, 2 to 10% of a hydrocolloid, water-soluble agents, and water; it is specified that the difference between the refractive indices of the aqueous and oil phases is no greater than 0.005. These jellies are intended for culinary or cosmetic use; it is specified that the hydrocolloid is gelatine and that the compositions contain not only citric acid, but also either a sugar or glycerol or sorbitol as water-soluble agent. In the Examples illustrating the invention, the prepared emulsions contain a maximum of only 70% by weight of oil phase, and the aqueous phase never contains less than 16% gelatine, or 4.8% by weight in terms of the final emulsion. It is moreover specified that it is essential, in order to prepare these emulsions with a high concentration of hydrophobic phase, to add the water-soluble surfactant agent at a concentration of 0.5 to 5.0% in terms of the jelly. Example 3 of this invention specifically describes a jelly which, for 70 parts Vaseline, contains 30 parts of an aqueous solution containing 29% water, 45% citric acid, 1% lauryl ether sulfate, and 25% gelatine, or for this latter constituent, 7.5% in terms of the weight of the final composition; this represents a significant protein input with regard to both nutrition and the consistency of the jelly, which probably is almost solid in texture.

With respect to the jellied laxative pharmaceutical preparations presented and listed in the Vidal dictionary (cited above), and regardless of the method for producing them, these products contain sucrose to improve their taste, which is noted as a contraindication to the treatment of constipation in diabetic patients or those on a strict hypocaloric diet. As regards the solid forms that are proposed, products in which the liquid oil is adsorbed onto a support, or is presented in microencapsulated form, are available commercially; these presentations require economically penalizing technologies.

Recently, in the European patent application published under no. 486 353, an anhydrous composition is proposed that is characterized by the incorporation of anhydrous lactulose into a mixture of purified paraffinic hydrocarbons whose melting point is between 45° C. and 60° C., the relative proportions of the constituents being such that the laxative activity of the hydrocarbons is said to be limited as compared to that of the lactulose, whose usual laxative activity is stated to be intensified in the claimed composition. A result of this kind would be worth confirming, since without further information it appears that in the proposed invention, the anhydrous lactulose is intimately mixed with a mixture of hydrocarbons whose melting point is much higher than the temperature of the human body, calling into serious question its availability in the gastrointestinal tract, and more generally the gustatory acceptability of the product. Moreover at present it cannot be considered that lactulose in its anhydrous form is an economically and practically satisfactory solution, given the technological outlay required to produce this product in its solid form and, in that state, its tendency to rehydrate spontaneously in the ambient environment.

In fact none of the solutions that have been proposed or marketed for administering paraffin oil for laxative purposes is entirely satisfactory, for practical, economic, or dietetic reasons.

SUMMARY OF THE INVENTION

The present invention resolves this situation by means of a hypocaloric jellied laxative composition with a high concentration of liquid paraffin oil associated with lactulose, which is a non-assimilable synthetic disaccharide that is itself acknowledged to have non-aggressive laxative properties.

Departing from the prior art and in particular with the teaching of French patent 2 618 351, the applicant has, surprisingly, produced emulsions which combine approximately 80% by weight of liquid paraffin oil with a sweetened aqueous phase containing lactulose and jellied by means of a hydrocolloid, this with the notable exclusion of any surfactant agent, in order to produce stable, homogeneous jellied compositions with a translucent appearance and a smooth, non-sticky texture.

DETAILED DESCRIPTION OF THE INVENTION

The object of the present invention is a new jellied, emulsified, and translucent composition characterized in that it consists essentially of 75 to 85 parts by weight of liquid paraffin oil and 25 to 15 parts by weight of a sweetened aqueous solution of lactulose containing a total of 54 to 66% by weight dry matter.

A preferred composition is one in which the liquid paraffin oil, whose refractive index is between 1.473 and 1.483, represents 76 to 80 parts by weight, for 20 to 24 parts by weight of an aqueous phase whose dry-matter content is 57.5 to 62.5%.

Aside from lactulose which is its major constituent, the aqueous phase also contains gelatin, organoleptic adjuvants, and optionally a non-assimilable carbohydrate.

A phase of this kind is produced by mixing 90 to 95 parts by weight of a lactulose syrup with 2.5 to 5.5 parts of a 20% aqueous solution of gelatin, 2 to 2.5 parts of a sweetening and coloring mixture, and optionally a non-assimilable carbohydrate, the dry-matter content conforming to the specifications indicated above and the refractive index of the mixture, determined at 20° C., matching that of the paraffin oil to within ±0.010 units.

More particularly, the lactulose syrup used corresponds to the grades currently available commercially, namely lactulose concentrations of 50 to 66%. A syrup titrating at 50% is preferred This is a clear, pale yellow syrup for which, at 20° C., the refractive index is between 1.430 and 1.490, rotatory power −36° to −44°, and density approximately 1.310.

The gelatin, meeting the specifications of the European Pharmacopeia (2nd ed.; 330, 1986), is used at a concentration of 0.5 to 1.1 parts by weight of the aqueous phase, and preferably 0.65 to 0.85 parts. The mixture intended to sweeten and color the composition comprises organoleptic adjuvants necessary for good presentation and good acceptability of the product, namely, expressed by weight in terms of the mixture, approximately 33% citric acid, approximately 60% of a flavoring composition which consists of a mixture of natural and/or artificial raspberry and plum flavors, approximately 5% of a synthetic sweetener such as saccharin sodium, and approximately 2% of a coloring agent such as cochineal red.

The non-assimilable or poorly assimilable carbohydrate additive that is used optionally to adjust the refractive index of the aqueous phase is selected from the class of mono- or disaccharides acknowledged as acceptable for pharmaceutical use and for administration to diabetic patients. The preferred compound is sorbitol, commonly used as an excipient and sweetener.

In particular when the dry-matter concentration or refractive index of the aqueous phase prepared in this manner prove to be less or greater than the standards defined above, they are adjusted by adding the carbohydrate to raise them, or conversely they are diluted with water to decrease them.

According to the invention, the particularly preferred composition corresponds to the following centesimal formula:

| | |
|---|---|
| Liquid paraffin oil | 78.230 g |
| 50% (by weight) lactulose syrup | 16.210 g |
| Powdered sorbitol | 4.200 g |
| Citric acid monohydrate | 0.150 g |
| Gelatin | 0.160 g |
| Cochineal red A coloring agent | 0.012 g |
| Composition of artificial and natural raspberry and plum flavors | 0.300 g |
| Saccharin sodium | 0.020 g |
| Potable water to make 100.000 g | |

The invention also relates to a method for preparing an oil-in-water emulsion of this kind, which consists in introducing the paraffin oil, heated to a temperature of 50° to 80° C., with appropriate agitation, into the aqueous phase which is also heated to a temperature of 40° to 70° C. and which comprises all the compounds of the aqueous phase except for the flavor composition, in order to produce a homogeneous and translucent jellied emulsion to which the flavoring composition is then added, and which is then transferred into a storage tank connected to the filling machines for distribution of the jelly into glass jars or single doses.

More precisely, the method consists in first dissolving the coloring agent in the freshly prepared gelatin solution, then adding it to the lactulose syrup in which the citric acid, the saccharin sodium, and optionally the sorbitol have previously been dissolved; then secondly preparing the actual emulsion, which consists in introducing the paraffin oil, previously brought to 50°–80° C. and preferably to 70° C.±5° C., into the aqueous phase prepared as described above, heated to 40°–70° C. and preferably to 55° C.±5° C. The flow rate, and consequently the time required for introduction, of the paraffin oil depend on the agitation efficacy and on the temperature at which the operation is performed. With "turbine" agitation, introduction can be performed in a time period of between 3 and 45 minutes. Under the preferred temperature conditions indicated above the operation can be performed, assuming effective agitation, in a period of between 5 and 20 minutes, after which the flavoring composition is introduced and the product yield is then transferred into a storage annex before dividing it into units intended for sale.

EXAMPLES

The examples and experiments described in the technical section below illustrate the invention and its implementation, but without thereby limiting it.

Example 1 (preferred)

Preparation of a jellied emulsion of centesimal composition:

| | |
|---|---|
| Liquid paraffin oil | 78.230 g |
| 50% (by weight) lactulose syrup | 16.210 g |
| Powdered sorbitol | 4.200 g |
| Citric acid monohydrate | 0.150 g |
| Gelatin | 0.160 g |
| Cochineal red A coloring agent | 0.012 g |
| Composition of artificial and natural raspberry and plum flavors | 0.300 g |
| Saccharin sodium | 0.020 g |
| Potable water to make 100.000 g | |

In a first step, 72.945 kg of 50% lactulose syrup that has previously been heated to 60° C.±5° C. is introduced into the apparatus intended for preparation of the emulsion, and 0.675 kg of citric acid monohydrate, 0.090 kg of saccharin sodium, and 18.900 kg of powdered sorbitol are then dissolved into it under moderate agitation.

Separately, 0.054 kg of cochineal red A is dissolved in 3.2 liters of potable water, into which 0.720 kg of gelatin meeting the specifications of the European Pharmacopeia (2nd ed.; 1986) is dispersed. The solution is left for 20 minutes to swell, and is then heated over a water bath to 55° C.±5° C. before adding it to the sweetened solution, as described previously, in the apparatus. The refractive index of the aqueous mixture, measured at 20° C., is 1.4740±0.010.

352.035 kg of liquid paraffin, previously heated to 70° C.±5° C., is then introduced continuously at a rate of 50±10 liters per minute with agitation, the agitation speed being gradually increased as introduction proceeds so as to ensure continuous incorporation of the added oil into the homogeneous jellied emulsion.

1.350 kg of a flavoring composition consisting of alcoholates of natural and artificial raspberry flavors and natural plum flavor is then added; agitation is continued for two minutes, then the emulsion is transferred into a storage tank connected to a packaging machine for subsequent distribution into glass jars or plastic cups for single doses.

The jelly prepared in this manner, after cooling to 20° C., is similar to a natural food jelly in its appearance, consistency, and transparency. The same is true for its handling during administration: it can be cut easily and cleanly with a spoon, and while being sufficiently firm not to flow off the implement, has a smooth texture with a pleasant gustatory feel.

Its stability, studied in glass jars at 20° C., is excellent: after 12 months its appearance, behavior, and organoleptic characteristics were completely retained.

Example 2

Using the method of Example 1, 86.850 kg of 66% (by weight) lactulose syrup, previously heated to 60° C.±5° C., is introduced into the apparatus intended for preparation of the emulsion, and 0.675 kg of citric acid monohydrate, then 0.090 kg of saccharin sodium, are then dissolved in this with moderate agitation.

Separately, 0.054 kg of cochineal red A is dissolved in 8.2 liters of potable water, in which 0.720 kg of gelatin is dispersed. After swelling, the solution is heated to 55° C.±5° C. over a water bath before adding it to the sweetened solution, thus producing an aqueous phase whose dry-matter content is 61%.

352.035 kg of liquid paraffin is then introduced into the mixture with agitation, as described in the previous Example, then 1.350 kg of a flavoring composition consisting of alcoholates of raspberry and plum flavors is added. After two minutes, the jellied emulsion is transferred into a storage tank before being distributed into units and packaged.

What is claimed is:

1. A jellied and translucent emulsion, characterized in that it consists essentially of about 75 to 85 parts by weight of liquid paraffin oil and 25 to 15 parts by weight of a sweetened aqueous solution of lactulose containing a total of 54 to 66% by weight dry matter.

2. The emulsion as defined in claim 1, consisting of 76 to 80 parts by weight of liquid paraffin oil with a refractive index between 1.473 and 1.483 and 24 to 20 parts by weight of a sweetened aqueous solution of lactulose containing a total of 57.5 to 62.5% by weight dry matter.

3. A jellied and translucent emulsion, characterized in that it consists essentially of about 75 to 85 parts by weight of liquid paraffin oil and 25 to 15 parts by weight of a sweetened aqueous solution of lactulose containing a total of 54 to 66% by weight dry matter, wherein the sweetened aqueous solution consists essentially of a mixture of 90 to 95 parts by weight of a lactulose syrup with 2.5 to 5.5 parts of a 20% aqueous solution of gelatin, 2 to 2.5 parts of a sweetening and coloring mixture, and optionally a non-assimilable carbohydrate, the refractive index of the said mixture, determined at 20° C., matching that of the paraffin oil to within ±0.010 units.

4. The emulsion as defined in claim 1, characterized in that the lactulose syrup used for preparation of the aqueous solution titrates at 50 to 66% by weight of product.

5. A jellied and translucent emulsion, characterized in that it consists essentially of about 75 to 85 parts by weight of liquid paraffin oil and 25 to 15 parts by weight of a sweetened aqueous solution of lactulose containing a total of 54 to 66% by weight dry matter and 0.5 to 1.1 parts by weight of gelatin meeting the specifications of the European Pharmacopeia (2nd ed.; 330, 1986).

6. A jellied and translucent emulsion, characterized in that it consists essentially of about 75 to 85 parts by weight of liquid paraffin oil and 25 to 15 parts by weight of a sweetened aqueous solution of lactulose containing a total of 54 to 66% by weight dry matter, and consisting essentially of a mixture of organoleptic adjuvants selected from the group consisting of citric acid, a flavoring composition of natural and/or artificial raspberry and plum flavors, saccharin sodium, and a coloring agent.

7. A jellied and translucent emulsion, characterized in that it consists essentially of about 75 to 85 parts by weight of liquid paraffin oil and 25 to 15 parts by weight of a sweetened aqueous solution of lactulose containing a total of 54 to 66% by weight dry matter, and consisting essentially of sorbitol as a carbohydrate additive to adjust the refractive index of the said solution.

8. The emulsion whose composition by weight is:

| | |
|---|---|
| Liquid paraffin oil | 78.230 g |
| 50% (by weight) lactulose syrup | 16.210 g |
| Powdered sorbitol | 4.200 g |
| Citric acid monohydrate | 0.150 g |
| Gelatin | 0.160 g |
| Cochineal red A coloring agent | 0.012 g |
| Composition of artificial and natural raspberry and plum flavors | 0.300 g |

| | |
|---|---|
| Saccharin sodium | 0.020 g |
| Potable water to make 100.000 g | |

9. A method for preparing a jellied, homogeneous, and translucent oil-in-water emulsion, which comprises introducing, over a time period of between 3 and 45 minutes, 75 to 85 parts by weight of paraffin oil whose temperature is from 50° to 80° C. into 25 to 15 parts of an aqueous phase, heated to a temperature of 40° to 70° C., comprising a mixture of 90 to 95 parts by weight of a lactulose syrup with 2.5 to 5.5 parts of a 20% aqueous solution of gelatin, 2 to 2.5 parts of a sweetening and coloring mixture, and optionally a non-assimilable carbohydrate, the refractive index of the said mixture, determined at 20° C., matching that of the paraffin oil to within ±0.010 units, then adding a flavoring composition and, after transfer, distributing the resulting jellied and translucent emulsion.

* * * * *